(12) United States Patent
Garcia-Ibanez

(10) Patent No.: US 11,478,546 B2
(45) Date of Patent: Oct. 25, 2022

(54) IMMUNOTHERAPY FOR THE TREATMENT OF ALLERGIC DISEASE

(71) Applicant: Roberto Garcia-Ibanez, Tampa, FL (US)

(72) Inventor: Roberto Garcia-Ibanez, Tampa, FL (US)

( * ) Notice: Subject to any disclaimer, the term of this patent is extended or adjusted under 35 U.S.C. 154(b) by 0 days.

(21) Appl. No.: 16/778,230

(22) Filed: Jan. 31, 2020

(65) Prior Publication Data

US 2020/0164063 A1  May 28, 2020

Related U.S. Application Data

(62) Division of application No. 15/912,904, filed on Mar. 6, 2018, now Pat. No. 10,603,376.

(60) Provisional application No. 62/552,054, filed on Aug. 30, 2017.

(51) Int. Cl.
| A61K 39/35 | (2006.01) |
| A61P 37/08 | (2006.01) |
| A61K 39/00 | (2006.01) |

(52) U.S. Cl.
CPC .............. *A61K 39/35* (2013.01); *A61P 37/08* (2018.01); *A61K 2039/54* (2013.01); *A61K 2039/542* (2013.01); *A61K 2039/545* (2013.01)

(58) Field of Classification Search
None
See application file for complete search history.

(56) References Cited

U.S. PATENT DOCUMENTS

| 8,491,909 B2 | 7/2013 | Esch |
| 9,271,899 B2 | 3/2016 | Francois |
| 9,481,716 B2 | 11/2016 | Clark et al. |
| 2009/0214597 A1* | 8/2009 | Moldt ..................... A61P 11/02 424/275.1 |

OTHER PUBLICATIONS

Allam et al. Immunologic response and safety in birch pollen sublingual versus oral vestibule immunotherapy: A pilot study. J. Allergy Clin Immunol. 1757-1759.e3 Available online May 1, 2014. http://dx.doi.org/10.1016/j.jaci.2014.03.026.*
Igarashi et al.'The Efficacy of Sublingual Immunotherapy for Allergic Rhinitis May Vary with the Time of Day.' IntArch Allergy Immunol 2016;171:111-118.*
ALLERCEPT Therapy Drops, Owner Workbook for Pets with Allergies; Heska Corporation; 2012.
Bird, Andrew J.; "Aimmune Therapeutics Announces Phase 2 Follow-On Study of AR101 for the Treatment of Peanut Allergy Demonstrated Increased Desensitization and Improved Tolerability With Low-Dose Maintenance"; Aimmune Therapeutics; Mar. 6, 2016; http://ir.aimmune.com/news-releases/news-release-details/aimmune.
Bollinger et al.; "Circadian Clocks in Mouse and Human CD4+ T Cells;" PloS One; vol. 6(12); e29801; https://doi.org/10.1371/journal.pone.0029801; 2011.
Cermakian et al.; "Crosstalk Between the Circadian Clock Circuitry and the Immune System"; Informa Health Care USA, Inc.; Early Online; pp. 1-19; 2013.
Cuesta et al.; "Simulated Night Shift Disrupts Circadian Rhythms of Immune Functions in Humans"; The Journal of Immunology; vol. 196; pp. 2466-2475; 2016.
Curtis et al.; "Circadian Clock Proteins and Immunity"; Immunity Review; vol. 40; pp. 178-186; Feb. 20, 2014.
Dimitrov et al.: "Number and Function of Circulating Human Antigen Presenting Cells Regulated by Sleep:" Sleep; vol. 30, No. 4; 2007.
Dumbell et al.; "Circadian Clocks, stress, and Immunity"; Frontiers in Endocrinology; vol. 7; Article 37; May 2016.
Krishna et al.; "Clinical Immunology Review Series: An Approach to Desensitization"; Clinical and Experimental Immunology; vol. 163; pp. 131-146; 2010.
Labrecque et al.; "Circadian Clocks in the Immune System"; Journal of Biological Rhythms; vol. 30, No. 4; pp. 277-290; Aug. 2015.
Lang et al.; "Shift of Monocyte Function Toward Cellular Immunity During Sleep;" Arch Intern. Med.; vol. 166; pp. 1695-1700; 2006.
Man et al.; "Immunity Around The Clock"; Sciencemag.org; vol. 354, Issue 6315; pp. 999-1003; Nov. 25, 2016.
Menachof, Michael; "Allergy Drops;" http://www.advancedentdenver.com/allergy/allergy-drops-faq; Oct. 6, 2017.
Okeehfe et al.; "NF-κB Signalling is Involved in Immune-Modulation, But Not Basal Functioning, of the Mouse Suprachiasmatic Circadian Clock": European Journal of Neuroscience; vol. 45; pp. 1111-1123; Feb. 23, 2017.
Plikus et al.; "The Circadian Clock in Skin: Implications for Adult Stem Cells, Tissue Regeneration, Cancer, Aging, and Immunity"; J. Biol Rhythms; vol. 30, No. 3; pp. 163-182; Jun. 1, 2016.
Scheiermann et al.; "Circadian Control of the Immune System"; National Institute of Health, National Rev. Immunol; vol. 13, No. 3; pp. 190-198; Mar. 2013.
Yu et al.; "Th17 Cell Differentiation is Regulated by the Circadian Clock"; National Institute of Health; vol. 342, No. 6159; pp. 727-730; Nov. 8, 2013.

* cited by examiner

*Primary Examiner* — Nora M Rooney
(74) *Attorney, Agent, or Firm* — Greenberg Traurig, P.A.; Stephen G. Anderson

(57) ABSTRACT

Compositions and methods for the treatment of allergic disease include treating a subject in need thereof with a dosage of an allergen, wherein the allergen is administered to the subject's oral vestibular space. In a preferred embodiment, the allergen is administered at night, thereby exploiting circadian rhythms in the subject's immune response and enhancing the effectiveness of the treatment.

6 Claims, 5 Drawing Sheets

IMMUNOTHERAPY FOR THE TREATMENT OF ALLERGIC DISEASE

CROSS REFERENCE TO RELATED APPLICATIONS

This application is a divisional of, and claims priority to and the benefit of, U.S. patent application Ser. No. 15/912,904, filed Mar. 6, 2018, which itself claims priority to, and the benefit of, U.S. Provisional Patent Application Ser. No. 62/552,054, filed Aug. 30, 2017, the contents of which is incorporated by reference and commonly owned.

FIELD OF THE INVENTION

The present invention generally relates to compositions and methods for the treatment of allergic disease.

BACKGROUND

Existing Immunotherapy Techniques

The rise in prevalence of allergic diseases is part of the new epidemic of non-communicable diseases associated with urbanization and progress, adoption of western lifestyles in developing countries, and exposure to various chemicals that are commonly used in current urban and developed environments. This rise in prevalence is associated with disruptions in the biome, excessive hygiene, and lack of exposure to natural environments such as barns, farms, and soil. Allergic diseases are thought to affect 20% to 30% of the population, but current numbers attest to an increase in the recent past. The cost of these diseases to society, healthcare systems, and affected individuals and their families is substantial.

The pharmacological treatment of allergic diseases includes use of over-the-counter antihistamines, decongestants, and intranasal steroids, prescription nasal steroids, and leukotriene receptor blockers. Domestic environmental intervention is designed to minimize exposure to indoor allergens, and when this fails or is insufficient, immunotherapy becomes the logical clinical step to follow.

The most widely used method of immunotherapy for the treatment of allergic disease is subcutaneous immunotherapy ("SCIT"), which utilizes allergen injections. This treatment method is invasive, painful, and time-consuming. Moreover, methods for subcutaneous immunotherapy administration have changed little since 1911. Injection-based methods typically consist of a buildup phase comprising about 100 to 400 separate injections over a period of 20 weeks (under ideal conditions with no interruptions or adverse reactions). Injection-based immunotherapy methods bear undesirable risks of adverse reactions that can be localized, generalized, near-fatal, or even fatal. In this context, improved methods of immunotherapy for treating allergic disease that are more amenable to modern lifestyles and carry much less risk to patients are needed.

Sublingual immunotherapy ("SLIT") is a somewhat newer treatment modality used to treat allergic disease. SLIT involves sublingual administration of a custom-formulated allergy serum over an extended period of time to gradually create immunity to a patient's specific allergic triggers. This form of immunotherapy is much less invasive than allergy shots and requires less nursing staff and office visits, as the majority of the treatment is self-administered by patients at home. Unfortunately, however, SCIT remains the preferred treatment by health insurance companies in the United States.

Circadian Rhythms and Components of the Immune System

Circadian rhythms recur in physiological, biochemical, metabolic, behavioral, and other parameters. Circadian rhythms cycle approximately every 24 hours and persist in the absence of external time cues. These internally-generated rhythms are the product of a complex circadian timing system with a master pacemaker located in the suprachiasmatic nuclei of the anterior hypothalamus, synchronizing semi-automatic circadian pacemakers throughout the central nervous system and the periphery in order to impose a daily temporal architecture on mammalian physiology and behavior. This system allows physiological and cellular functions to be coordinated in time for both energy conservation processing and for the time segregation of opposing processes.

Circadian rhythmicity also affects the function of the immune system with variations of immunocompetent cells and cytokines and assuring a well-timed anticipatory organization of biological processes that play a critical role in the preservation of homeostasis and defense. At the intracellular end, circadian clocks are regulated by a set of clock genes activated by transcription factors CLOCK and BAML1.

For example, T and B lymphocyte concentrations are considerably higher at night. CD4+(T helper) and CD8+ (cytotoxic)-naïve, central memory, and effector memory T lymphocytes show peak numbers at night, whereas CD4+ effector T cells show no rhythm and CD8+ effector T cells show a low-amplitude rhythm with peaks during the day. Granulocytes, monocytes, and natural killer cells have shown their numbers to peak midday or late in the day. Serum levels and in vitro production of interferon gamma (IFN-γ), tumor necrosis factor alpha (TNF-α), and IL-1, IL-2, IL-6, and IL-12 peak at night or early in the morning.

Antigen presenting cells (APCs) are involved in the capture and processing of allergens and the subsequent presentation of pathogen-derived peptides to native T cells in the lymph nodes, tonsils, and adenoids. APCs are located in the superficial layers of the oral mucosa and consist of CD 207+ Langerhans cells and CD 11b+, CD 68+, and CD206+ macrophages located in the lamina propria. APCs capture allergens by phagocytosis and by IgE mediation, as they are FcεR1 positive. APCs exhibit a tolerogenic phenotype in that they produce IL-10 and TGF 13, and they express indoleamine 2,3-dioxygenase. Macrophages secrete IL-10 and IL-12 and express retinaldehyde dehydrogenase 2 as a consequence in the absence of danger signals. The default response of oral APCs to allergens is intolerance as opposed to inflammation within the induction of IFN-γ producing and IL-10 secreting TH-1 and regulatory T cells (Tregs), respectively, in draining cervical lymph nodes.

Sleep supports the immunological synapse between APC and the T cells in lymph nodes. During sleep, there is increased production of pro-inflammatory Th1-supporting hormones such as melatonin, GH, prolactin, and leptin, whereas anti-inflammatory hormones such as cortisol and catecholamine reach a nadir. This pro-inflammatory hormonal boost during sleep acts like an adjuvant, presumably on APCs, which show a sleep-dependent production of IL-12, which in turn supports Th1 lineage commitment (Dimitrov et al., 2007; Lange et al., 2006, 2011). The regulatory role of APCs mediating the sleep-associated peak of T cell cytokine production is substantiated by the fact that the rhythm in cytokine production of isolated CD4+ T cells is shifted by several hours (Bollinger et al., 2011).

In contrast, the initiation of a Th1 immune response that evolves more slowly requiring the interaction between APC and T cell in lymph nodes, protein biosynthesis, and cell proliferation is supported during sleep. The Th1 response is energy consuming and involves the release of pro-inflammatory mediators associated with pain, immobility, and malaise; therefore, its timing to the sleep period seems reasonable. B and T cells harbor an intrinsic clock, but additional regulatory influences of sleep, locomotor activity, hormonal changes, and APC activity entrain the rhythm of lymphocyte numbers and functions. In many, but not all in vivo studies, adaptive immune responses such as the delayed-type hypersensitivity reaction, as well as the T cell and antibody response to immunizations, benefit from sleep. Such a time-limited boost of lymphocyte activity may serve immune homeostasis and maximize efficiency of the immune system.

Oral Immunological Milieu

The oral cavity contains an abundance of immunologically-active tissues (tonsils, adenoids, and lymph nodes). This expedites the process of efficient antigen presentation. The low concentration of mast cells guarantees safe allergen administration via vestibular immunotherapy. According to Allam (Allergy 2008), there is a substantial concentration of dendritic cells in the oral vestibular space.

There is no current literature, guidelines, or recommendations regarding the management in patients who do not tolerate or have failed to respond to SCIT. Commonly, treatment is interrupted and patients continue to experience symptoms managed only with pharmacotherapy. Thus, there remains a need in the art for improved compositions and methods for treating allergic disease. The embodiments disclosed herein are aimed at overcoming these and other needs in the art.

SUMMARY

The inventor of the embodiments disclosed herein discovered a new and improved method for treating allergic disease, which includes, inter alia, treating a patient at night using the compositions and methods described herein. The inventor also discovered that treating a patient at night via the oral vestibular space is an ideal protocol for the delivery of allergen-specific immunotherapy and other immunologic intervention.

Embodiments of the present disclosure include a method for treating an allergic disease, the method comprising administering daily to a person in need thereof a first dosage of an allergen, the first dosage applied to the person's sublingual space and progressively increasing in concentration per day over a time period of about four weeks; and administering daily to the person a second dosage of the allergen, the second dosage applied to the person's oral vestibular space and remaining at a constant concentration per over a time period of about twelve weeks; wherein the administering steps comprise administering the allergen at night.

Another embodiment of the present disclosure includes a method for treating allergic disease, the method comprising providing a serum to a patient, the serum including at least one allergen; and instructing the patient to self-administer at night a dosage of the serum, the instructing including defining a treatment period having a first phase and a second phase, wherein the dosage progressively increases during the first phase, and wherein the dosage remains constant during the second phase; wherein in the first phase the patient self-administers the serum to its sublingual space, and wherein in the second phase the patient self-administers the serum to its oral vestibular space.

DETAILED DESCRIPTION OF EMBODIMENTS

Figure 1:
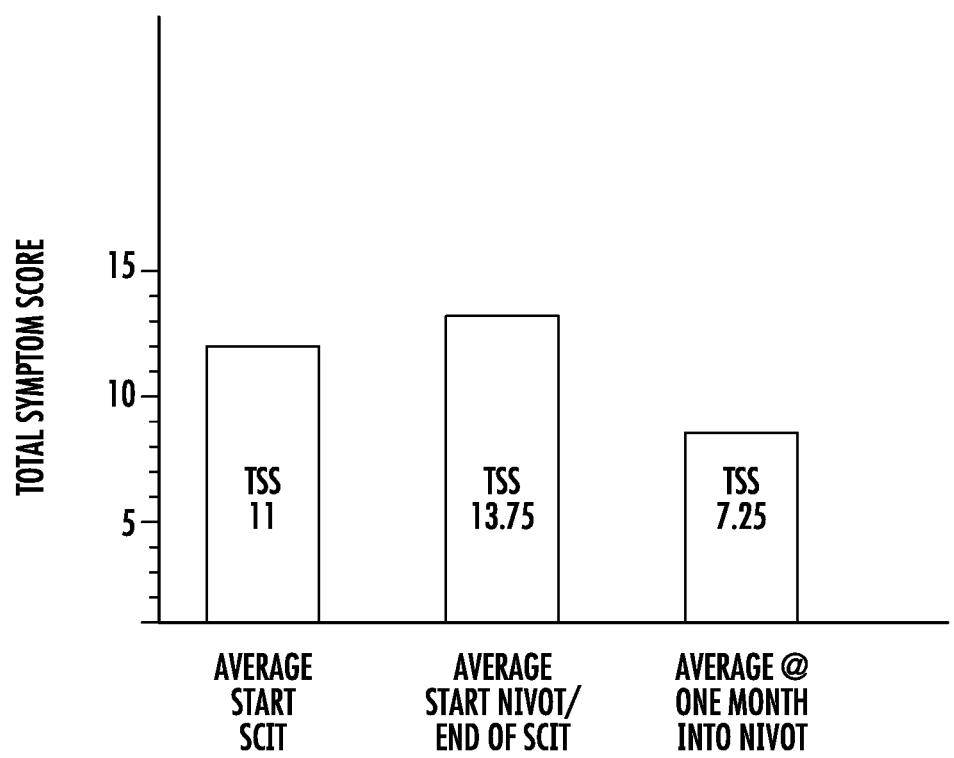
FIG. 1 is a depiction of a reduction in the total symptom score in patients treated in accordance with embodiments of the present disclosure.

The present invention will now be described more fully hereinafter with reference to the accompanying drawings, in which embodiments of the invention are shown by way of illustration and example. This invention may, however, be embodied in many forms and should not be construed as limited to the embodiments set forth herein. Rather, these embodiments are provided so that this disclosure will be thorough and complete, and will fully convey the scope of the invention to those skilled in the art.

The inventor discovered that embodiments of the present disclosure, as herein referred to as Nocturnal Immuno Vestibular Oral Therapy ("NIVOT"), are best delivered in two phases: (1) buildup and (2) maintenance. In one embodiment, administration requires a four-week build-up stage, during which incremental dosages are administered in the sublingual spaces. Alternatively, the build-up stage spans about one week, about two weeks, about three weeks, about five weeks, about six weeks, or any other time period deemed suitable depending upon the needs of the patient being treated. During this initial stage, patients hold the drops under the tongue for at least 10 minutes before swallowing, however other retention times are considered to be within the scope of the present disclosure. In a preferred embodiment, the dosages are delivered to the sublingual space during the buildup stage and later delivered to the vestibular space during a subsequent maintenance phase. Nocturnal administration, for example, after sundown or otherwise determined upon consideration of the circadian rhythm(s) and sleep cycle(s) of a patient to be treated, maximizes the benefits of the natural immunological circadian cycles and minimizes disruption of the attachment of allergens in the mixture from the oral mucosa by eating or drinking.

Thus, embodiments of the present disclosure include a method for treating a person with allergic disease, the method comprising administering to the person's sublingual space a first dosage of an allergen; and administering to the person's oral vestibular space a second dosage of the allergen. In one embodiment, the allergen is administered at night so as to maximize the effectiveness of the treatment by exploiting the circadian rhythmicity of the patient's immune system and reductions in oral mucosal disruptions during sleep.

As is typical with known immunotherapeutic treatments for allergic disease, a concentration of the first dosage of the allergen may be increased over time, thereby permitting a gradual increase in the patient's tolerance to the allergen. In this first treatment phase, the first dosage of the allergen may be administered over a time period of about 4 weeks. The second dosage of the allergen, administered during a second phase of the treatment, remains constant over time. By way of example, the second dosage is administered over a time period of about 12 weeks.

Another embodiment includes a method for treating allergic disease, the method comprising providing an allergen to a person, and instructing the person to self-administer the allergen at night. The instructing may include defining a treatment period having a first phase and a second phase, wherein in the first phase the person self-administers the allergen to its sublingual space, and wherein in the second phase the person self-administers the allergen to its oral vestibular space. In the first phase, a dosage of the allergen progressively increases. In the second phase a dosage of the allergen is constant. As with the first embodiment disclosed, the first phase spans a time period of about 4 weeks, and the second phase spans a time period of about 12 weeks.

Yet another embodiment includes a method for treating allergic disease, the method comprising administering an allergen to a subject's oral vestibular space. Alternatively, the treatment may be self-administered by the subject thereof. In a self-administration protocol, the method includes providing an allergen to a subject, and instructing the subject to administer the allergen to an oral vestibular space. Further, the physician or other health professional may instruct subject to only administer the allergen at night.

Still yet another embodiment includes a method for treating an allergic disease, the method comprising providing an allergen to a person, and instructing the person to administer the allergen in accordance with a treatment plan, the treatment plan having a first phase and a second phase, the first phase including administering the allergen to the person's sublingual space, the second phase including administering the allergen to the person's oral vestibular space.

It will be understood by one of ordinary skill that time points for nocturnal administration of an allergen may vary, so long as the administration is timed to correlate with the subject's immune system circadian cycles and/or sleep cycles as herein described or as otherwise understood in the art.

The allergen may be any known allergen. By way of non-limiting example, the allergen may be at least one of a grass, an inhalant, a weed, a tree, a mold, or any other substance or extract thereof that causes an allergic reaction in a subject. For example, the grass allergen may be a component of, or extract from, a grass such as Bahia, Bermuda, Johnson, Rye, or Timothy grass, or any other known grass and/or an extract therefrom. Exemplary inhalants include D. Farinea, D. Pteronyssinus, cat epithelium, dog epithelium, and/or German or American cockroach. Exemplary weeds include short ragweed, marsh elder, dog fennel, mugwort, baccharis, lambs quarter, spiny pigweed, sheep sorrel, nettle, and/or English plantain. Exemplary trees include Virginia live oak, red cedar, bald cypress, Australian pine, Bayberry, sweet gum, box elder, American elm, E. sycamore, and/or red mulberry. Exemplary molds include alternaria, penicillum mix, Cladosporium, Aspergillus mix, Helminithosporium, Curvularia, Fusarium, Epicoccum, Pullularia, Hormodendrum, horse, and/or rabbit.

Exemplary Dosage Regimen

By way of non-limiting example, an embodiment of the present disclosure may be prepared and administered in accordance with the following procedure. Vials 1 and 2 of the custom formulated serum are administered in progressively increasing dosages during the first 2 weeks of treatment. Similarly, vials 3 and 4 are administered in progressively increasing dosages during weeks 3 and 4 of treatment. Vial 5, or "maintenance", is started on week 5 and continues for the duration of treatment with daily administration. The maintenance vials last for 3 months.

Once maintenance dosage is reached, administration is relocated to the oral vestibular space, which is the area between the buccal mucosa and the teeth. It extends posteriorly all the way to the 2nd and 3rd molar regions. This space is rich in dendritic cells, which are central antigen presenting cells for the immune processing of antigens. The maintenance dosage is one drop per vial per day, which is very easily accommodated in this small space. Patients are instructed to hold the drops in place for at least 10 to 20 minutes. Afterward, patients are instructed to move the retained allergen and saliva to the inner aspects of the upper and lower lips and buccal mucosa.

The administration of oral immunotherapy has well-documented attachment of radiolabeled allergen to the sublingual mucosa that persists even after 24 hours of administration. Diurnal administration of vestibular immunotherapy is affected by drinking and eating, and this has led us to the use of nocturnal administration. We have associated vestibular administration of allergen mixes after the patient has completed the nightly oral hygiene process with improved efficacy that is evident in a relatively short period of time (1 month).

This substantial modification allows the allergens to remain undisturbed in the vestibular mucosa for at least 8 hours, therefore allowing APCs and macrophages to have access to allergens without displacement by eating or drinking. Additionally, the potential of an immunological circadian cycle with better immunological efficiency during sleep clearly plays a role in the efficacy of nocturnal vestibular immunotherapy.

Interruptions in treatment of less than 6 weeks are inconsequential and maintenance dosages can be resumed with no adverse effects. There have been no observed episodes of anaphylaxis or other adverse events with the embodiments disclosed. This modality of immunotherapy is very safe and well tolerated. In contrast, interruptions in SCIT become a very difficult clinical situation with no studies to show that the maintenance dose may be safely resumed without potential adverse effects.

The embodiments disclosed are believed to induce a decrease in eosinophilic infiltrates and allergen-specific Th2 CD 4+ T cell responses in target organs in parallel with induction of systemic Th1 and Treg responses, a decrease in specific IgE in serum and mucosa, and induction of allergen-specific IgA and IgG2. Thus, successful immunotherapy may be correlated with immune reorientation of existing allergen-specific Th2 responses toward Th1 and Treg protide. The embodiments disclosed also likely induce expression of C1q and stabilize in the blood of responders patients as well as down-regulation of markers of type 2 DC (CD141 and OX-402).

Exemplary Preparation of Treatment Sets.

In one embodiment of the present disclosure, new NIVOT treatment sets comprising four 10 mL vials filled with allergens formulated specifically to each patient's specific allergies according to skin testing (or any other determination) are prepared in accordance with the following protocol.

Prior to starting, clean the work area with a surface disinfectant. Collect all the supplies needed for the creation of the treatment sets, including 10 mL empty vials, 5 mL empty scratch dropper vials, 1 mL 23 G×½-inch mixing syringes, 5 mL syringe with an 18 G×1-inch needle, 100 mL bottle of 50% glycerin diluent, 4×4-inch cotton pads, and 70% isopropyl rubbing alcohol.

Before allergen stocks are created, all 50 mL allergen serum bottles and all 10 mL vials are disinfected with a 4×4-inch cotton pad soaked in rubbing alcohol. In a first 10 mL vial (vial A), a possible total of 13 separate extracts of allergens consisting of grasses and some weeds are mathematically divided into equal portions to fill a 10 mL vial. A second 10 mL vial (vial B), includes extracts of the rest of the weeds and all of the trees (a possible total of 12 allergens) and are again mathematically divided into equal portions to fill a 10 mL vial. In a third vial (vial C), a possible total of 11 extracts of allergens consisting of molds and cockroach mix (if applicable) are mathematically divided into equal portions to fill a 10 mL vial. In a fourth vial (vial D), a possible total of four extracts of allergens consisting of inhalants including cat, dog, and dust mites are mathematically divided into equal portions to fill a 10 mL vial. These 10 mL vials (vials A, B, C, and D) are hereinafter referred to as "stock" and can be used in the future to make additional maintenance compositions.

Exemplary Dilution Protocol.

Allergen stocks may be obtained from any commercial allergen supplier. After the stocks are made, they are lined up vertically starting from the bottom. The bottom vial is labeled as vial A and the top as vial D.

Starting in the column next to the stocks, place five 5 mL unused empty dropper vials horizontally in order with the vial next to the stock ("maintenance") being the least dilute, or strongest, and the vial farthest from the stock as the most dilute, or weakest. In total, every new patient receives up to 20 empty scratch dropper vials.

The four 5 mL vials next to the 10 mL stock vials initially remain empty, as these vials will only contain allergen serum, not diluent. They are labeled "maintenance." A first vial is labeled vial #4 and will contain a 1:1 dilution. Fill each vial in that column with 0.75 mL of diluent by extracting 0.75 mL of diluent from the diluent bottle using a 1 mL mixing syringe with an attached 23 G×½-inch needle and dispensing 0.75 mL of diluent into each of the 4 vials (A through D, if applicable).

Starting from left to right, are vials labeled #3, which will contain a dilution of 1:10, vials labeled #2 which will contain a dilution of 1:100, and finally vials labeled #1 which will contain a dilution of 1:1000. Fill each of these vials with 2.25 mL of diluent by extracting 2 mL from the diluent bottle using a 5 mL mixing syringe with an attached 23 G×½-inch needle and then extracting 0.25 mL from the diluent bottle using a 1 mL mixing syringe with an attached 23 G×½-inch needle. Dispense the full 2.25 mL of diluent into each of the sets of vials labeled #1 through #3 (A though D, if applicable, for each set).

After the diluent is inserted into all of the vials, the final step of the dilution process is adding the stock to the vials by extracting 0.75 mL of stock A using a 1 mL mixing syringe with a 23 G×½-inch needle attached and dispensing 0.75 mL of stock into vial #4A for a dilution of 1:1. Repeat the process by extracting the same amount from stocks B, C, and D (if applicable) and dispensing it into the vials of set #4B, C, and D (if applicable).

Using a new 1 mL mixing syringe with a 23 G×½-inch needle attached, extract 0.25 mL of stock A and dispense it into the #3A vial for a dilution of 1:10. Repeat this process, extracting the same amounts from stocks B, C, and D (if applicable) and dispensing into the vials of set #3B, C, and D (if applicable).

Using a 1 mL mixing syringe with a 23 G×½-inch needle attached, extract 0.25 mL of the mixed contents of vial #3A and dispense it into vial #2A for a dilution of 1:100. You will repeat this process extracting the same amount from #2 B, C, and D (if applicable) and dispensing into the vials of set #3 B, C, and D (if applicable).

Using a 1 mL mixing syringe with an attached 23 G×½-inch needle, extract 0.25 mL of the mixed contents of vial #2A and dispense it into vial #1A for a dilution of 1:1000. Repeat this process with all of the vials in the #1 set (B, C, and D if applicable).

Using a 5 mL syringe with an attached 18 G×1-inch needle, extract 4.9 mL of stock A and dispense it into the empty dropper vial labeled #5A (also known as MAINT-1-DROP-DAILY) for a dilution of 1:01. Repeat this process, extracting the same amounts from stock B, C, and D (if applicable) and dispensing into the vials of set #5 B, C, and D (if applicable). The vials in set #5 are used for the patient's first set of maintenance, which can last up to 3 months.

Exemplary Storage Procedure.

After the dilutions are all finalized, they are ready to be packaged and refrigerated. Each set of vials is packaged in a 13 mm box with a 13 mm tray insert that can hold up to 6 vials. Each box will contain vials from the same dilutions and stock. There will be five boxes made per patient for each new treatment. Box 1 will contain all of the vials from set #1 (1:1000), vials A through D (if applicable). Box 2 will contain all of the vials from set #2 (1:100), vials A through D (if applicable). Box 3 will contain all of the vials from set #3 (1:10), vials A through D (if applicable). Box 4 will contain all of the vials from set #4 (1:1), vials A through D (if applicable). Box 5 will contain all of the vials from set #5 "maintenance" (1.01), vials A through D (if applicable).

Each box is labeled with the patient's first and last name, what number vial the box contains (#1, #2, etc.), and the expiration date of the vials. Each box will also have a red warning label that reads: "Keep out of reach of children. Keep refrigerated." All boxes may be held together by a rubber band and must be refrigerated at 40° Fahrenheit or less at all times. Boxes should only be removed from the refrigerator when in use for treatment.

Alternative Embodiment

In another embodiment, a new patient comes in for an allergy checkup. The patient is then scheduled for follow up visit, which involves skin test. The results of the skin test aid in a determination of what allergens the patient is allergic to. This skin test, in turn, informs the physician of which allergens to include in the treatment regimen. Thus, the identity of the allergens will be different for each patient depending on what they are allergic to.

In one embodiment, the patient will have another follow up visit to pick up the drops (total 4 vials). The first vial drop may be administered at the clinic under a physician's observation. If the patient is able to tolerate this first dosage without an adverse reaction, this first dosage will become the patient's starter dose. If the patient has an adverse reaction to the starter dose, the starter dose is diluted and the procedure is initiated again. The first four vials are in increasing dosage and will last about one month.

Once the patient is able to tolerate the drops we will start them on Maintenance dose after 1st month. This dosage will continue for 12 months.

EXAMPLES

A chart retrospective review has been conducted on four patients with allergic rhinitis and one with asthma who were initially managed by Subcutaneous Immunotherapy (SCIT). These patients were treated with SCIT for an average of 11 months and due to lack of response were later switched to Nocturnal Immuno Vestibular Oral Therapy (NIVOT). Symptoms were quantified using the Total Symptom Score (TSS), a standard that is well known in the art.

With reference to FIG. 1, the four patients experienced an average increase in TSS of 2.75 points while on SCIT. Within the first month of treatment in accordance with an embodiment of the present disclosure, an average decrease in TSS of 6.5 points was measured. One of the patients was affected with asthma and was frustrated with lack of response while on SCIT. In this case, after introduction to treatment in accordance with an embodiment of the present disclosure, we did not see a decrease in TSS but her Asthma Control Test (ACT) score improved by 12 points 1 month after the introduction of NIVOT with no changes made to her asthma controller medications. NIVOT was tolerated without any adverse events in all four patients.

Figure 2:
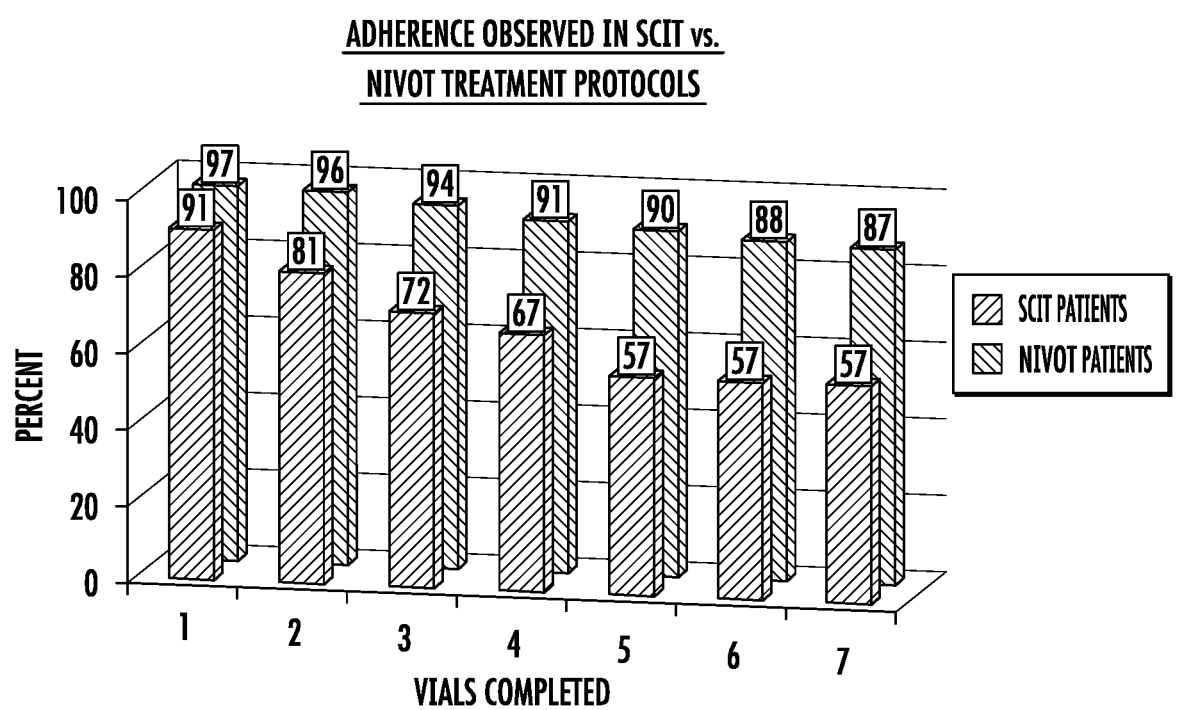
FIG. 2 is a depiction of increased adherence to treatment in patients treated in accordance with embodiments of the present disclosure.

FIG. 2 depicts patients' improved adherence to the treatment protocol of the present disclosure as compared to adherence to treatment regimens by patients treated with SCIT. After 7 weeks of treatment, 87% of the patients treated in accordance with embodiments of the present disclosure were still adhering to the treatment protocol, whereas only 57% present of patients treated with SCIT were still undergoing treatment. In fact, improved adherence to treatment can be measured at as early as one week after initiation of the treatment protocol.

Figure 3B:
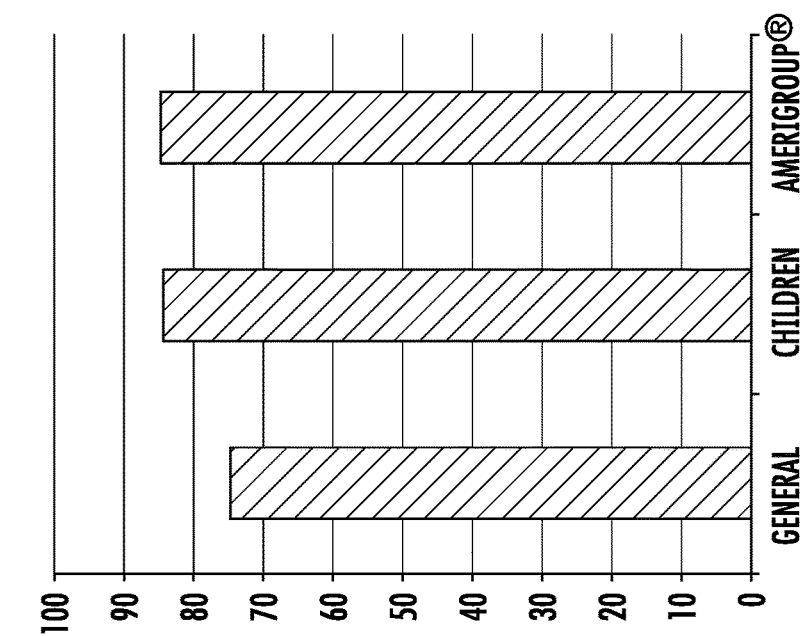
FIGS. 3A and 3B are depictions of a reduction in the total symptom score and adherence levels, respectively, in patients treated in accordance with embodiments of the present disclosure.
Figure 3A:
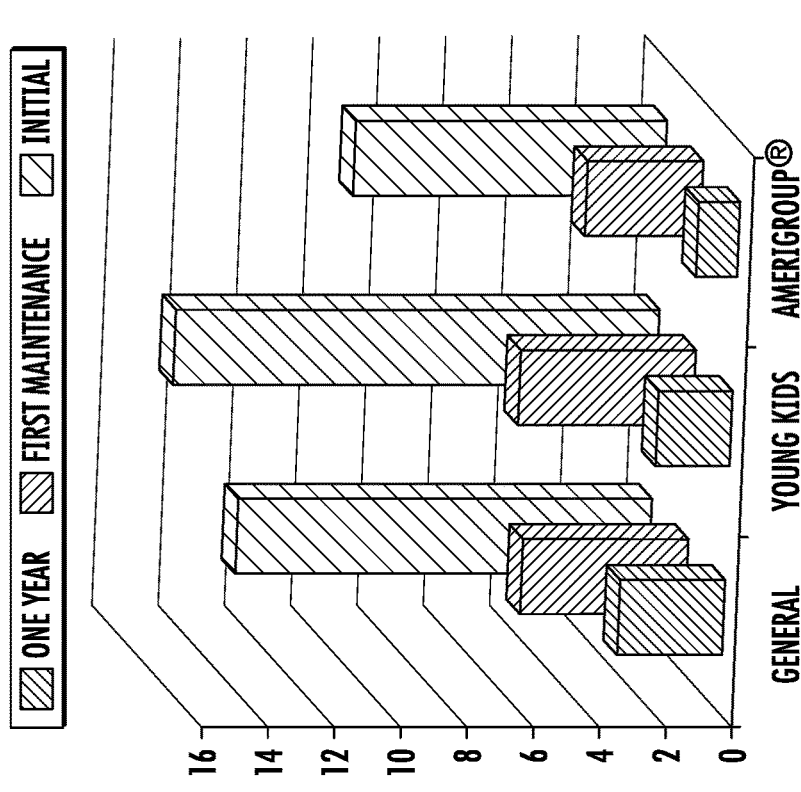

FIG. 3A is a comparison of total symptom score between the general population, children, and Amerigroup® patients. The first maintenance doses were provided at one month after the start of treatment. As depicted, all three groups showed a substantial decrease in total symptom score, and that decrease was maintained for at least one year following the initiation of treatment in accordance with the embodiments of the present disclosure. As depicted in FIG. 3B, adherence levels for patients in this study were also within a desirable range.

Figure 4:
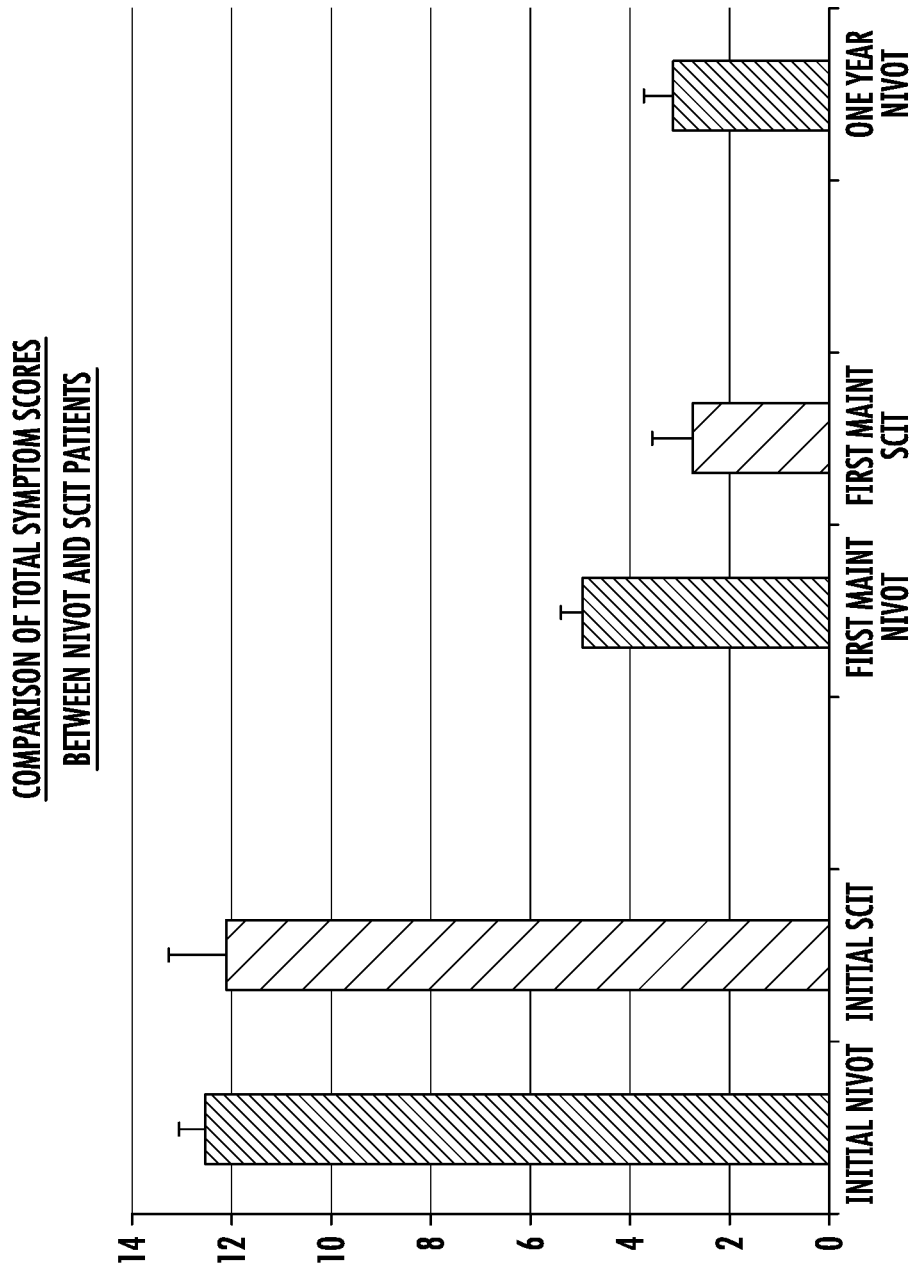
FIG. 4 is a comparison of total symptom score changes between patients treated with prior art methods and patients treated in accordance with embodiments of the present disclosure.

FIG. 4 is a comparison of total symptom scores between patients treated with the embodiments disclosed herein and patients treated with traditional SCIT. Patients in the two treatment groups each began treatment at a TSS of about 12-13. At the beginning of the first maintenance dose, patients exhibited comparable decreases in TSS. We observed an even further decrease in TSS at least one year after treatment.

Figure 5:
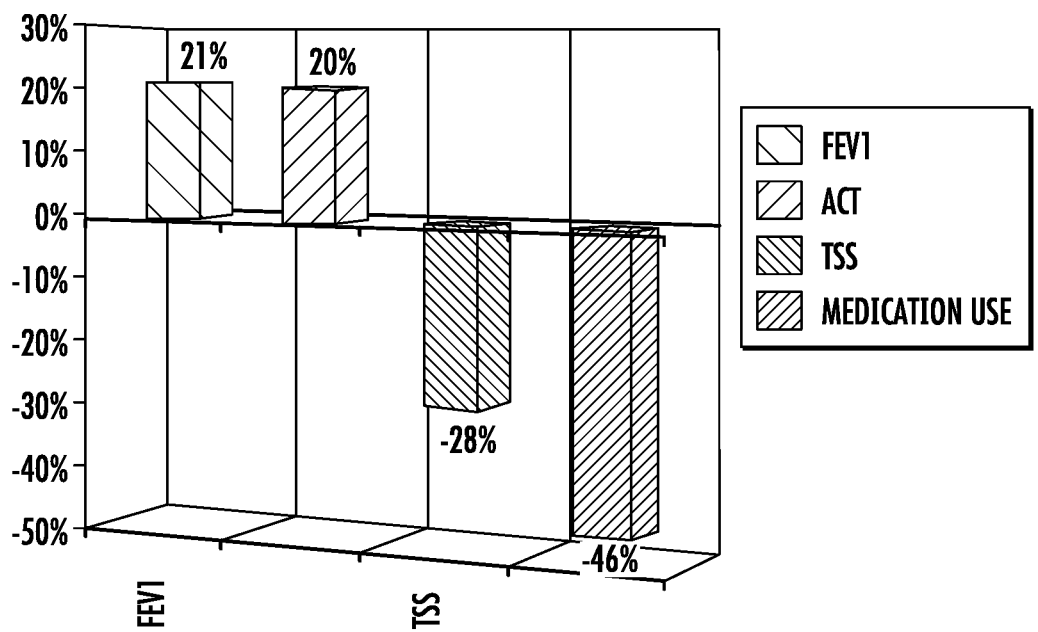
FIG. 5 depicts changes in clinical parameters in 38 patients from inner city asthmatic patients treated with embodiments of the present disclosure.

FIG. 5 depicts changes in clinical parameters in 38 patients from inner city asthmatic patients treated with embodiments of the present disclosure (FEV1: Forced Expiratory Volume in the first second of a pulmonary function test ("PFT"), wherein the amount of air blown in 1 second is measured; ACT: Asthma Control Test (commercially available); TSS: total symptom score).

In patients who fail to respond to SCIT, NIVOT administered at bedtime should be considered as a viable alternative in the management of these patients. Nocturnal administration may have an impact on the effectiveness of NIVOT due to immunological changes associated with the circadian cycle of the immune system.

Although the invention has been described relative to various selected embodiments herein presented by way of example, there are numerous variations and modifications that will be readily apparent to those skilled in the art in light of the above teachings. It is therefore to be understood that, within the scope of the claims hereto attached and supported by this specification, the invention may be practiced other than as specifically described.

What is claimed is:

1. A method for treating allergic disease, the method comprising:
   administering an allergen directly to a sublingual space; and
   administering the allergen directly to an oral vestibular space;
   wherein at least one of the administering steps is performed at night.

2. The method of claim 1, wherein the administering steps are performed in accordance with a protocol having a first phase and a second phase.

3. The method of claim 1, wherein the administering an allergen directly to a sublingual space comprises administering the allergen in multiple doses over a first period of time.

4. The method of claim 3, wherein a concentration of the allergen increases over the first period of time.

5. The method of claim 1, wherein the administering the allergen directly to an oral vestibular space comprises administering the allergen in multiple doses over a second period of time.

6. The method of claim 5, wherein a concentration of the allergen remains constant over the second period of time.

* * * * *